(12) United States Patent
Veslocki

(10) Patent No.: US 8,491,461 B1
(45) Date of Patent: Jul. 23, 2013

(54) PROPHYLACTIC PROSTHESIS ASSEMBLY

(76) Inventor: Peter Veslocki, Old Saybrook, CT (US)

( * ) Notice: Subject to any disclaimer, the term of this patent is extended or adjusted under 35 U.S.C. 154(b) by 183 days.

(21) Appl. No.: 13/269,860

(22) Filed: Oct. 10, 2011

(51) Int. Cl.
*A61F 5/00* (2006.01)

(52) U.S. Cl.
USPC .......................................... 600/38; 128/844

(58) Field of Classification Search
USPC ................... 600/38–41; 128/842–844
See application file for complete search history.

(56) References Cited

U.S. PATENT DOCUMENTS

| | | | |
|---|---|---|---|
| 991 A | 10/1838 | Lewis | |
| 829 A | 10/1846 | Guild | |
| 4,432,357 A | 2/1984 | Pomeranz | |
| 4,920,983 A * | 5/1990 | Jimenez et al. | 128/844 |
| 5,024,852 A * | 6/1991 | Busnel et al. | 427/2.3 |
| 5,509,891 A | 4/1996 | DeRidder | |
| 5,513,652 A | 5/1996 | Schwartz | |
| 6,840,244 B2 | 1/2005 | Kemp | |
| D591,853 S | 5/2009 | Osterberg | |
| 7,604,588 B2 | 10/2009 | Nguyen | |
| 2008/0185008 A1 | 8/2008 | Ou | |

* cited by examiner

*Primary Examiner* — John Lacyk

(57) ABSTRACT

A prophylactic prosthesis assembly for assisting in providing the semblance of an erection includes a body that has a first end, a second end, and a perimeter wall that extends between the first and second ends. The perimeter wall forms a hollow cylinder and each of the first and second ends is open. A two part epoxy includes a plurality of first compounds and a plurality of second compounds positioned discretely in the first and second channels. The body is comprised of a resiliently stretchable material. A head has an attached end, a free end and an exterior wall. The body has a penis removably inserted into it and the body is deformed and compressed to mix together the first and second compounds such that the body becomes semi-rigid after the first and second compounds chemically react to form a thermosetting polymer.

4 Claims, 4 Drawing Sheets

PROPHYLACTIC PROSTHESIS ASSEMBLY

FIELD OF THE DISCLOSURE

The disclosure relates to prophylactic prosthesis devices and more particularly pertains to a new prophylactic prosthesis device for assisting in providing the semblance of an erection.

SUMMARY OF THE DISCLOSURE

An embodiment of the disclosure meets the needs presented above by generally comprising a body that has a first end, a second end, and a perimeter wall that extends between the first and second ends. The perimeter wall includes an inner surface and an outer surface. The perimeter wall forms a hollow cylinder and each of the first and second ends is open. The body includes a plurality of first channels that are positioned between the inner and outer surfaces. A plurality of second channels is positioned between the inner and outer surfaces and intersects the first channels to define a plurality of intersections. A two part epoxy includes a plurality of first compounds and a plurality of second compounds positioned discretely in the first and second channels. The body is comprised of a resiliently stretchable material. A head has an attached end, a free end and an exterior wall. The exterior wall forms a hollow hemisphere that has the attached end open and the free end at a pole of the hemisphere. The attached end has a same diameter as and is attached to and coextensive with the first end. The head is comprised of a resiliently stretchable material. Wherein the body is configured to have a penis removably inserted therein and the body is deformed and compressed to mix together the first and second compounds such that the body becomes semi-rigid after the first and second compounds chemically react to form a thermosetting polymer.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
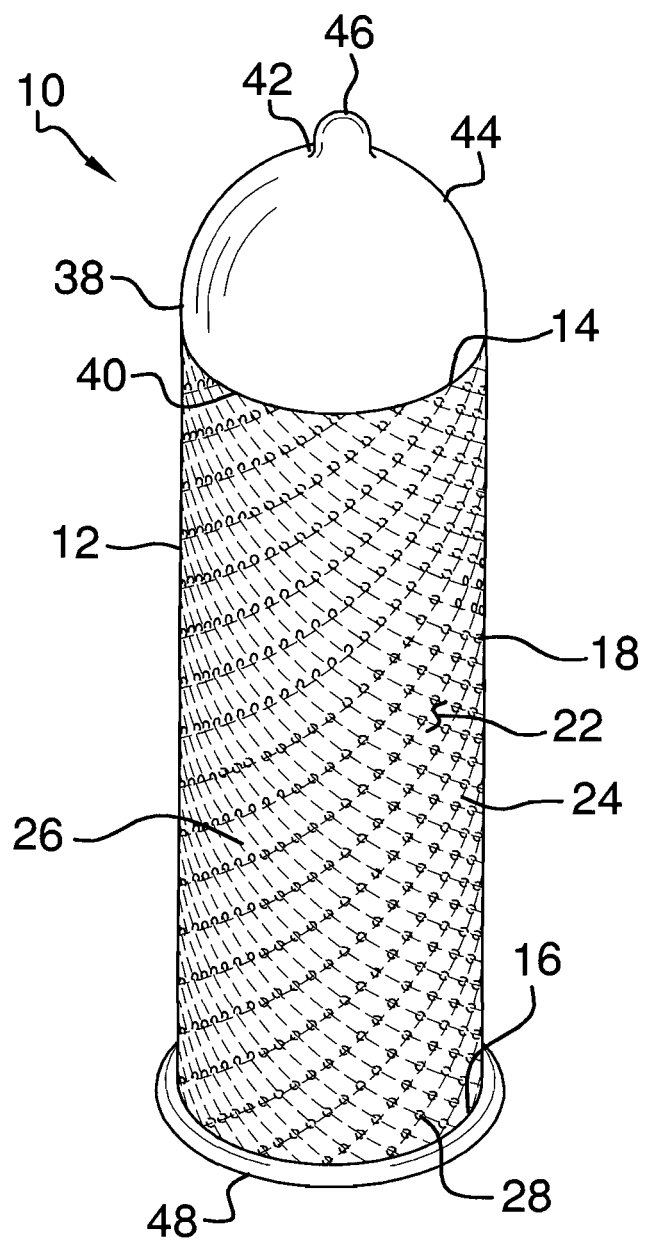
FIG. 1 is a top perspective view of a prophylactic prosthesis assembly according to an embodiment of the disclosure.
Figure 2:
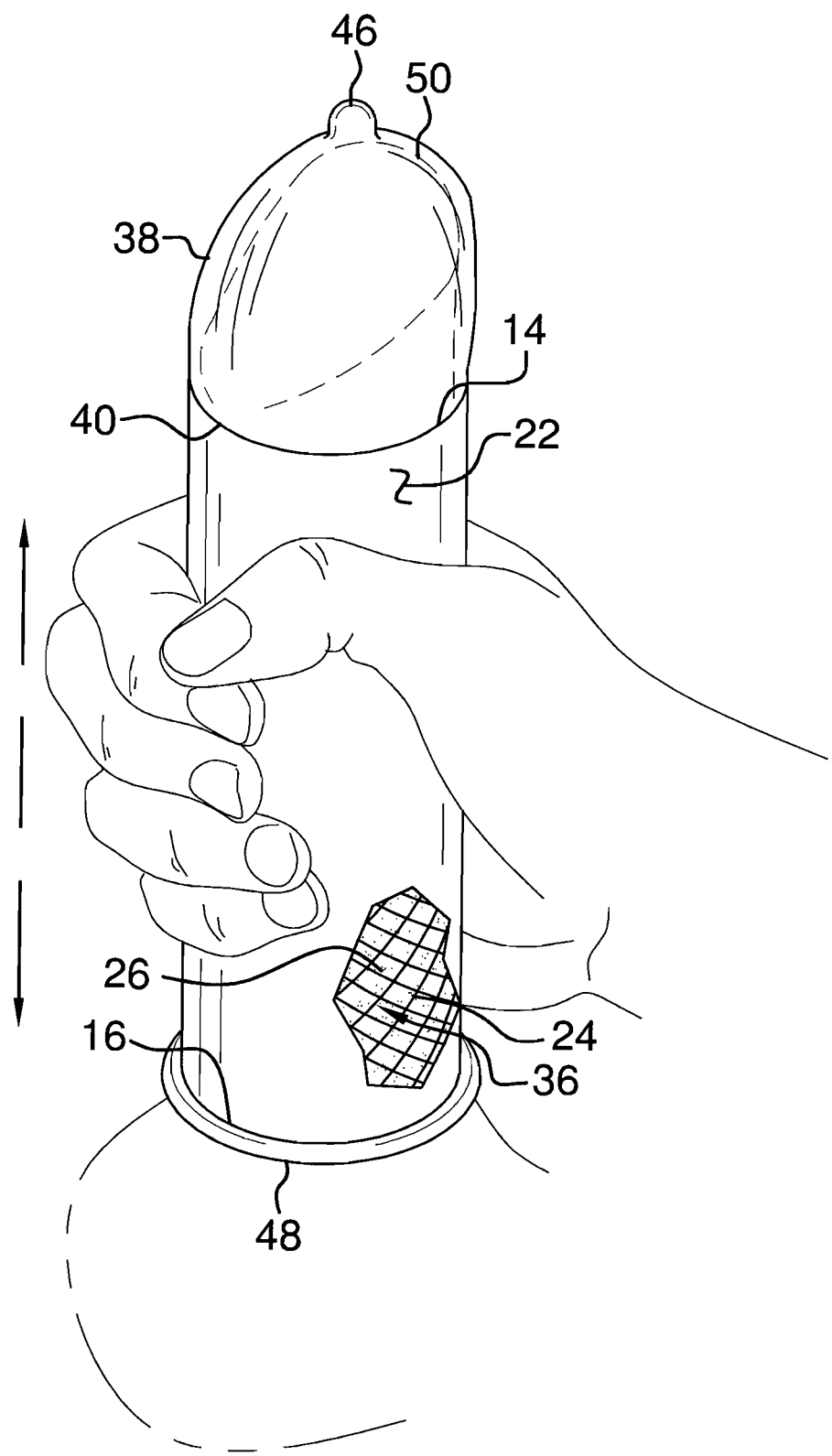
FIG. 2 is a broken in-use view of an embodiment of the disclosure.
Figure 3:
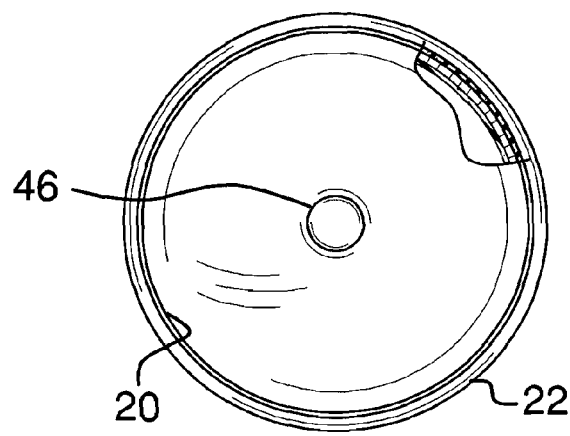
FIG. 3 is a broken top view of an embodiment of the disclosure.
Figure 4:
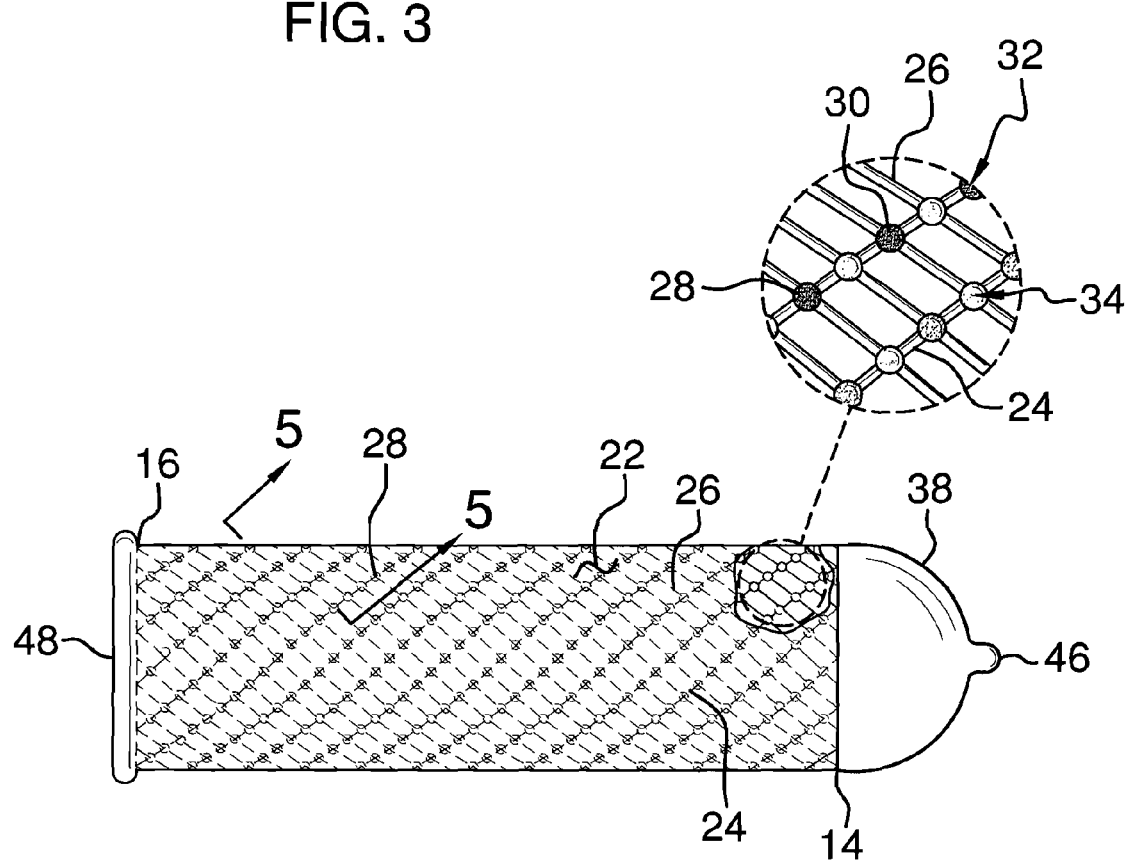
FIG. 4 is a broken side view of an embodiment of the disclosure.
Figure 5:
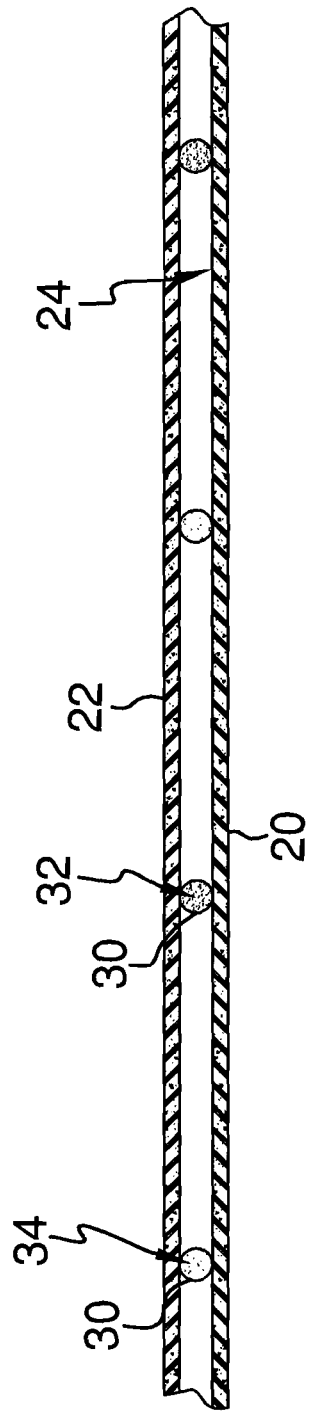
FIG. 5 is a cross-sectional view taken from line 5-5 of FIG. 4 of an embodiment of the disclosure.

With reference now to the drawings, and in particular to FIGS. 1 through 5 thereof, a new prophylactic prosthesis device embodying the principles and concepts of an embodiment of the disclosure and generally designated by the reference numeral 10 will be described.

As best illustrated in FIGS. 1 through 5, the prophylactic prosthesis assembly 10 generally comprises a body 12 that has a first end 14, a second end 16, and a perimeter wall 18 extending between the first 14 and second 16 ends. The perimeter wall 18 includes an inner surface 20 and an outer surface 22. The perimeter wall 18 forms a hollow cylinder that has each of the first 14 and second 16 ends open. The body 12 is comprised of a resiliently stretchable material such as latex, rubber or other similar material.

The body 12 includes a plurality of first channels 24 that are positioned between the inner 20 and outer 22 surfaces. The first channels 24 are curvilinear from the first end 14 to the second end 16 and define hollow tubes. A plurality of second channels 26 is positioned between the inner 20 and outer 22 surfaces and the second channels 26 define hollow tubes. The second channels 26 are curvilinear from the first end 14 to the second end 16 in an opposite direction from the first channels 24 such that the first 24 and second 26 channels intersect in a cross-hatching pattern to define a plurality of intersections 28. The first 24 and second 26 channels are in communication with one another as well as being in communication with the plurality of intersections 28.

A plurality of capsules 30 is positioned in the body 12 with each of the intersections 28 containing one of the capsules 30. The capsules 30 are each breakable, particularly when pressure is applied to them. A two part epoxy is provided that includes a plurality of first compounds 32 and a plurality of second compounds 34. Each of the capsules 30 has one of the first 32 or second 34 compounds therein. The first 32 and second 34 compounds may be distributed evenly throughout the plurality of intersections 28 so that half of the capsules 30 contain the first compound 32 and half of the capsules 30 contain the second compound 34.

The first 32 and second 34 compounds are positioned at alternating ones of the intersections 28 of the first 24 and second 26 channels with respect to each other. Each of the first 32 and second 34 compounds is in communication with associated ones of the first 24 and second 26 channels when the capsules 30 are broken. When the capsules 30 are broken each of the first 32 and second 34 compounds may travel throughout the first 24 and second 26 channels so the first 32 and second 34 compounds can be mixed. The first compound 32 may comprise a resin and the second compound 34 may comprise a hardener which, when mixed together, forms a conventional thermosetting polymer 36. The thermosetting polymer 36 may be cured at ambient temperature over a period of time of less than 5 minutes.

A head 38 is provided that has an attached end 40, a free end 42 and an exterior wall 44. The exterior wall 44 forms a hollow hemisphere that has the attached end 40 being open and the free end 42 at a pole of the hemisphere. The attached end 40 has a same diameter as and is attached to and coextensive with the first end 14. The free end 42 has a reservoir 46 extending upwardly from the exterior wall 44. The reservoir 46 is used for retaining ejaculated semen. The head 38 may be comprised of a resiliently stretchable material such as latex, rubber, or other similar material. A loop 48 is attached to and is coextensive with the second end 16. The loop 48 may retain the second end 16 in an open position.

The body 12 is configured to have a penis 50 removably inserted therein via the second end 16. After the penis 50 is inserted the body 12 is deformed and compressed to break the capsules 30 and mix together the first 32 and second 34 compounds such that the body 12 becomes semi-rigid after the first 32 and second 34 compounds chemically react to form a thermosetting polymer 36.

In use, an erect penis 50 is inserted into the body 12 via the second end 16. The body 12 may be massaged such that the capsules 30 break and the first 32 and second 34 compounds are distributed through and mixed within the first channels 24, the second channels 26 and the plurality of intersections 28. The first 32 and second 34 compounds may form a thermosetting polymer 36 that may simulate an erect penis 50.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A prophylactic prosthesis assembly configured for assisting in providing the semblance of an erection, said assembly comprising:
   a body having a first end, a second end, and a perimeter wall extending between said first and second ends, said perimeter wall including an inner surface and an outer surface, said perimeter wall forming a hollow cylinder having each of said first and second ends being open, said body including;
   a plurality of first channels being positioned between said inner and outer surfaces;
   a plurality of second channels being positioned between said inner and outer surfaces and intersecting said first channels to define a plurality of intersections;
   a two part epoxy including a plurality of first compounds and a plurality of second compounds positioned discretely in said first and second channels;
   said body being comprised of a resiliently stretchable material;
   a head having a attached end, a free end and an exterior wall, said exterior wall forming a hollow hemisphere having said attached end being open and said free end being at a pole of said hemisphere, said attached end having a same diameter as and being attached to and coextensive with said first end, said head being comprised of a resiliently stretchable material; and
   wherein said body is configured to have a penis removably inserted therein and said body is deformed and compressed to mix together said first and second compounds such that said body becomes semi-rigid after said first and second compounds chemically react to form a thermosetting polymer.

2. The assembly according to claim 1, wherein:
   said first channels are curvilinear from said first end to said second end, said first channels defining hollow tubes; said second channels are curvilinear from said first end to said second end in an opposite direction from said first channels such that said first and second channels intersect in a cross-hatching, said second channels defining hollow tubes.

3. The assembly according to claim 1, further including a plurality of capsules being positioned in said body, each of said intersections containing one of said capsules, said capsules each being breakable, each of said capsules having one of said first or second compounds therein, said first and second compounds being positioned at alternating ones of said intersections of said first and second channels with respect to each other, each of said first and second compounds being in communication with associated ones of said first and second channels when said capsules are broken.

4. A prophylactic prosthesis assembly configured for assisting in providing the semblance of an erection, said assembly comprising:
   a body having a first end, a second end, and a perimeter wall extending between said first and second ends, said perimeter wall including an inner surface and an outer surface, said perimeter wall forming a hollow cylinder having each of said first and second ends being open, said body including;
   a plurality of first channels being positioned between said inner and outer surfaces, said first channels being curvilinear from said first end to said second end, said first channels defining hollow tubes;
   a plurality of second channels being positioned between said inner and outer surfaces, said second channels being curvilinear from said first end to said second end in an opposite direction from said first channels such that said first and second channels intersect in a cross-hatching pattern to define a plurality of intersections, said second channels defining hollow tubes;
   a plurality of capsules being positioned in said body, each of said intersections containing one of said capsules, said capsules each being breakable;
   a two part epoxy including a plurality of first compounds and a plurality of second compounds, each of said capsules having one of said first or second compounds therein, said first and second compounds being positioned at alternating ones of said intersections of said first and second channels with respect to each other, each of said first and second compounds being in communication with associated ones of said first and second channels when said capsules are broken;
   said body being comprised of a resiliently stretchable material;
   a head having a attached end, a free end and an exterior wall, said exterior wall forming a hollow hemisphere having said attached end being open and said free end being at a pole of said hemisphere, said attached end having a same diameter as and being attached to and coextensive with said first end, said free end having a reservoir extending upwardly from said exterior wall, said head being comprised of a resiliently stretchable material;
   a loop being attached to and being coextensive said second end; and
   wherein said body is configured to have a penis removably inserted therein and said body is deformed and compressed to break said capsules and mix together said first and second compounds such that said body becomes semi-rigid after said first and second compounds chemically react to form a thermosetting polymer.

* * * * *